United States Patent [19]
Alesi et al.

[11] Patent Number: 5,779,130
[45] Date of Patent: Jul. 14, 1998

[54] SELF-CONTAINED POWERED SURGICAL APPARATUS

[75] Inventors: Daniel E. Alesi, Sherman; Robert J. Geiste, Milford; Dominick L. Mastri, Bridgeport, all of Conn.; Wayne P. Young, Brewster, N.Y.; Kenneth E. Toso, Wilton, Conn.

[73] Assignee: United States Surgical Corporation, Norwalk, Conn.

[21] Appl. No.: 319,907

[22] Filed: Oct. 7, 1994

Related U.S. Application Data

[63] Continuation-in-part of Ser. No. 287,455, Aug. 5, 1994, abandoned.

[51] Int. Cl.$^6$ .................................................. A61B 17/068
[52] U.S. Cl. .......................... 227/176.1; 227/178.1; 227/180.1; 227/19
[58] Field of Search .......................... 227/175.1, 176.1, 227/178.1, 179.1, 180.1, 19

[56] References Cited

U.S. PATENT DOCUMENTS

| | | |
|---|---|---|
| 1,881,250 | 10/1932 | Tomlinson . |
| 3,618,842 | 11/1971 | Bryan . |
| 3,815,476 | 6/1974 | Green et al. . |
| 3,952,748 | 4/1976 | Kaliher et al. . |
| 4,071,029 | 1/1978 | Richmond et al. . |
| 4,289,131 | 9/1981 | Mueller . |
| 4,334,539 | 6/1982 | Childs et al. . |
| 4,484,503 | 11/1984 | Sitte et al. . |
| 4,489,724 | 12/1984 | Arnegger . |
| 4,494,057 | 1/1985 | Hotta . |
| 4,520,817 | 6/1985 | Green . |
| 4,605,001 | 8/1986 | Rothfuss et al. . |
| 4,610,383 | 9/1986 | Rothfuss et al. . |
| 4,644,952 | 2/1987 | Patipa et al. . |
| 4,650,460 | 3/1987 | Roizenblatt . |
| 4,655,673 | 4/1987 | Hawkes . |
| 4,705,038 | 11/1987 | Sjostrom et al. . |
| 4,733,118 | 3/1988 | Mihalko . |
| 4,771,774 | 9/1988 | Simpson et al. . |
| 4,784,137 | 11/1988 | Kulik et al. . |

(List continued on next page.)

FOREIGN PATENT DOCUMENTS

| | | |
|---|---|---|
| 0156774 | 10/1985 | European Pat. Off. . |
| 0216532 | 4/1987 | European Pat. Off. . |
| 0536903 | 4/1993 | European Pat. Off. . |
| 0539762 | 5/1993 | European Pat. Off. . |
| 0552050 | 7/1993 | European Pat. Off. . |
| 0593920 | 4/1994 | European Pat. Off. . |
| 0598579 | 5/1994 | European Pat. Off. . |
| 0621006 | 10/1994 | European Pat. Off. . |
| 0634144 | 1/1995 | European Pat. Off. . |
| 2660851 | 10/1991 | France . |
| 2903159 | 7/1980 | Germany . |
| 3114135 | 10/1982 | Germany . |
| 4213426 | 10/1992 | Germany . |
| 659146 | 4/1979 | U.S.S.R. . |
| 9308754 | 5/1993 | WIPO . |
| 9314706 | 8/1993 | WIPO . |

*Primary Examiner*—Scott A. Smith

[57] ABSTRACT

A self-contained powered surgical stapling device is provided which includes an elongate body and a disposable cartridge assembly detachably supported in a distal end portion of the body. The cartridge assembly includes a frame configured to engage the distal end portion of the body, a housing supported within the frame and containing a plurality of surgical fasteners, an anvil mounted for movement with respect to the housing, an actuation assembly configured to translate relative to the housing and the anvil to progressively move the anvil from an open position to a closed position and to sequentially eject the surgical fasteners from the housing to be formed against the anvil, and an axial drive screw mounted in the frame and threadably associated with the actuation assembly for effectuating the longitudinal translation thereof. A motor assembly having an axial drive shaft is disposed within the elongate body, and a coupling is provided for detachably connecting the axial drive shaft and the axial drive screw. A power source is disposed within the elongate body for energizing the motor assembly.

20 Claims, 16 Drawing Sheets

U.S. PATENT DOCUMENTS

| | | |
|---|---|---|
| 4,867,158 | 9/1989 | Sugg . |
| 4,887,599 | 12/1989 | Muller . |
| 4,936,845 | 6/1990 | Stevens . |
| 4,995,877 | 2/1991 | Ams et al. . |
| 5,040,715 | 8/1991 | Green et al. . |
| 5,059,203 | 10/1991 | Husted . |
| 5,071,430 | 12/1991 | de Salis et al. . |
| 5,133,359 | 7/1992 | Kedem . |
| 5,133,713 | 7/1992 | Huang et al. . |
| 5,133,729 | 7/1992 | Sjostrom . |
| 5,170,925 | 12/1992 | Madden et al. . |
| 5,192,292 | 3/1993 | Cezana et al. . |
| 5,201,750 | 4/1993 | Hocherl et al. . |
| 5,207,697 | 5/1993 | Carusillo et al. . |
| 5,221,279 | 6/1993 | Cook et al. . |
| 5,237,884 | 8/1993 | Seto . |
| 5,249,583 | 10/1993 | Mallaby . |
| 5,258,007 | 11/1993 | Spetzler et al. . |
| 5,261,877 | 11/1993 | Fine et al. . |
| 5,268,622 | 12/1993 | Philipp . |
| 5,289,963 | 3/1994 | McGarry et al. . |
| 5,312,023 | 5/1994 | Green et al. . |
| 5,318,221 | 6/1994 | Green et al. . |
| 5,326,013 | 7/1994 | Green et al. . |
| 5,467,911 | 11/1995 | Tsuruta et al. . |

SELF-CONTAINED POWERED SURGICAL APPARATUS

CROSS-REFERENCE TO RELATED APPLICATIONS

This application is a continuation-in-part of copending application Ser. No. 08/287,455 filed Aug. 5, 1994, now abandoned, the contents of which are incorporated herein by reference.

BACKGROUND

1. Technical Field

A self-contained powered surgical stapling apparatus is provided for sequentially applying a plurality of surgical fasteners to body tissue and optionally incising the fastened tissue.

2. Background of Related Art

Surgical devices wherein tissue is first grasped or clamped between opposing jaw structure and then joined by means of surgical fasteners are well known in the art. In some instruments a knife is provided to cut the tissue which has been joined by the fasteners. The fasteners are typically in the form of surgical staples however, two part polymeric fasteners are also utilized.

Instruments for this purpose can include two elongated members which are respectively used to capture or clamp tissue. Typically, one of the members carries a disposable cartridge which houses a plurality of staples arranged in at least two lateral rows while the other member includes an anvil which defines a surface for forming the staple legs as the fasteners are driven from the cartridge. Generally, the stapling operation is effected by a pusher which travels longitudinally through the cartridge carrying member, with the pusher acting upon the staples to sequentially eject them from the cartridge. A knife may travel with the pusher between the staple rows to longitudinally cut and/or open the stapled tissue between the rows of staples. Such instruments are disclosed in U.S. Pat. No. 3,079,606 to Bobrov et al. and U.S. Pat. No. 3,490,675 to Green.

A later stapler disclosed in U.S. Pat. No. 3,499,591 to Green applies a double row of staples on each side of the incision. This is accomplished by providing a cartridge assembly in which a cam member moves through an elongate guide path between two sets of staggered staple carrying grooves. Staple drive members are located within the grooves and are positioned in such a manner so as to be contacted by the longitudinally moving cam to effect ejection of the staples.

Each of the instruments described above were designed for use in conventional surgical procedures wherein surgeons have direct manual access to the operative site. However, in endoscopic or laparoscopic procedures, surgery is performed through a small incision or through narrow a cannula inserted through small entrance wounds in the skin. In order to address the specific needs of endoscopic and/or laparoscopic surgical procedures, an endoscopic surgical stapling apparatus has been developed and is disclosed in U.S. Pat. No. 5,040,715. This apparatus is well suited for such procedures and includes a fastener applying assembly having an anvil and a staple cartridge provided at the distal end of an endoscopic body portion which permits the instrument to be inserted into a cannula and be remotely operated by the surgeon through manipulation of a proximal handle mechanism.

The instruments discussed above all require some degree of manually applied force in order to clamp, fasten and/or cut tissue. Surgeons have thus recognized the benefits of using self-powered instruments that are actuable with only a limited degree of physical force. Self-powered surgical instruments have been provided to serve these needs and include both gas powered surgical staplers, as shown, for example, in U.S. Pat. No. 5,312,023, and electrically powered surgical instruments as described in U.S. Pat. Nos. 4,635,638 and 5,258,007, and European Pat. Appln. No. 0 552 050. In general, prior art electrically powered surgical instruments have been driven by external power sources. The instruments were connected to the power sources by conductive cables. Such cables could, however, become entangled during a surgical procedure, thereby complicating the operation.

It would be beneficial to provide a self-contained powered surgical apparatus for applying a plurality of surgical staples to body tissue and concomitantly incising the stapled tissue. Such an apparatus should be compact, lightweight and easy to manufacture. Currently, surgical instruments are designed for use in either open, i.e. invasive procedures, or endoscopic/laparoscopic procedures. As noted above, endoscopic instruments require elongate shafts to access remote surgical sites. Conventional surgical instruments are not constructed in this manner. It would be advantageous to provide a powered surgical instrument which can be readily adapted for use in both conventional and laparoscopic procedures.

SUMMARY

A self-contained powered surgical apparatus for applying a plurality of surgical fasteners to body tissue is provided. The apparatus includes an elongate instrument body defining a longitudinal axis, a cartridge assembly housing a plurality of surgical fasteners, and an anvil member mounted adjacent the cartridge assembly and configured for movement with respect thereto between an open and a closed position.

The apparatus further includes a motor assembly disposed within the elongate instrument body, an actuating assembly driven by the motor assembly for effectuating progressive closure of the anvil and sequential ejection of the surgical fasteners and a power source disposed within the body for energizing the motor assembly. Preferably, the actuating assembly includes a drive member which is threadably associated with an axial drive screw that is driven by the motor assembly.

In a preferred embodiment, the actuating assembly includes a first camming mechanism configured to move the anvil member into a closed position to clamp tissue, and a second camming mechanism configured to sequentially eject fasteners from the cartridge as it translates therethrough. A tissue cutting member is preferably associated with the actuating assembly for translating through the cartridge assembly to incise the stapled body tissue. A control for the motor assembly to operate the powered surgical apparatus preferably includes first and second control buttons for effecting distal and proximal movement of the actuating assembly.

In one embodiment, the powered surgical apparatus includes an elongate shaft configured to engage with a proximal end of the main instrument body to facilitate utilization of the apparatus during an endoscopic procedure. Preferably, the extension shaft interacts with the motor control buttons at the proximal end of the main instrument body to operate the apparatus from a location remote from the surgical site.

In another embodiment the powered surgical apparatus is intended to be employed during a laparoscopic procedure by providing a mechanical hand which is configured to extend into the abdominal cavity through a cannula and be remotely manipulated to actuate the apparatus.

In another embodiment, the powered surgical apparatus includes an elongate body defining a longitudinal axis, and a disposable cartridge assembly which is detachably supported in a distal end portion of the elongate body.

The disposable cartridge assembly includes a frame having a proximal end portion configured to engage the distal end portion of the elongate body, and a housing supported within the frame and containing a plurality of surgical fasteners. An anvil member is pivotably associated with the frame and is mounted for movement with respect to the housing between an open position and a closed position. An actuation assembly is disposed within the frame and is configured to translate in a longitudinal direction relative to the housing and the anvil to progressively move the anvil from the open position to the closed position and sequentially eject the surgical fasteners from the housing to be formed against the anvil. An axial drive screw is rotatably mounted within the frame and threadably associated with the actuation assembly for effectuating the longitudinal translation thereof The surgical apparatus further includes a motor assembly having an axial drive shaft, and a coupling to detachably connect the axial drive screw of the cartridge assembly to the axial drive shaft of the motor. A power source is disposed within the elongate body for energizing the motor assembly. Preferably, a bayonet-type fitting is associated with the distal end portion of the elongate body and the proximal end portion of the frame to facilitate the detachable connection of the cartridge assembly.

Further features of the powered surgical apparatus will become more readily apparent to those skilled in the art from the following detailed description of the invention taken in conjunction with the drawings.

BRIEF DESCRIPTION OF THE DRAWINGS

Various embodiments of the powered surgical apparatus will be described hereinbelow with reference to the drawings wherein.

DETAILED DESCRIPTION OF PREFERRED EMBODIMENTS

Figure 1:
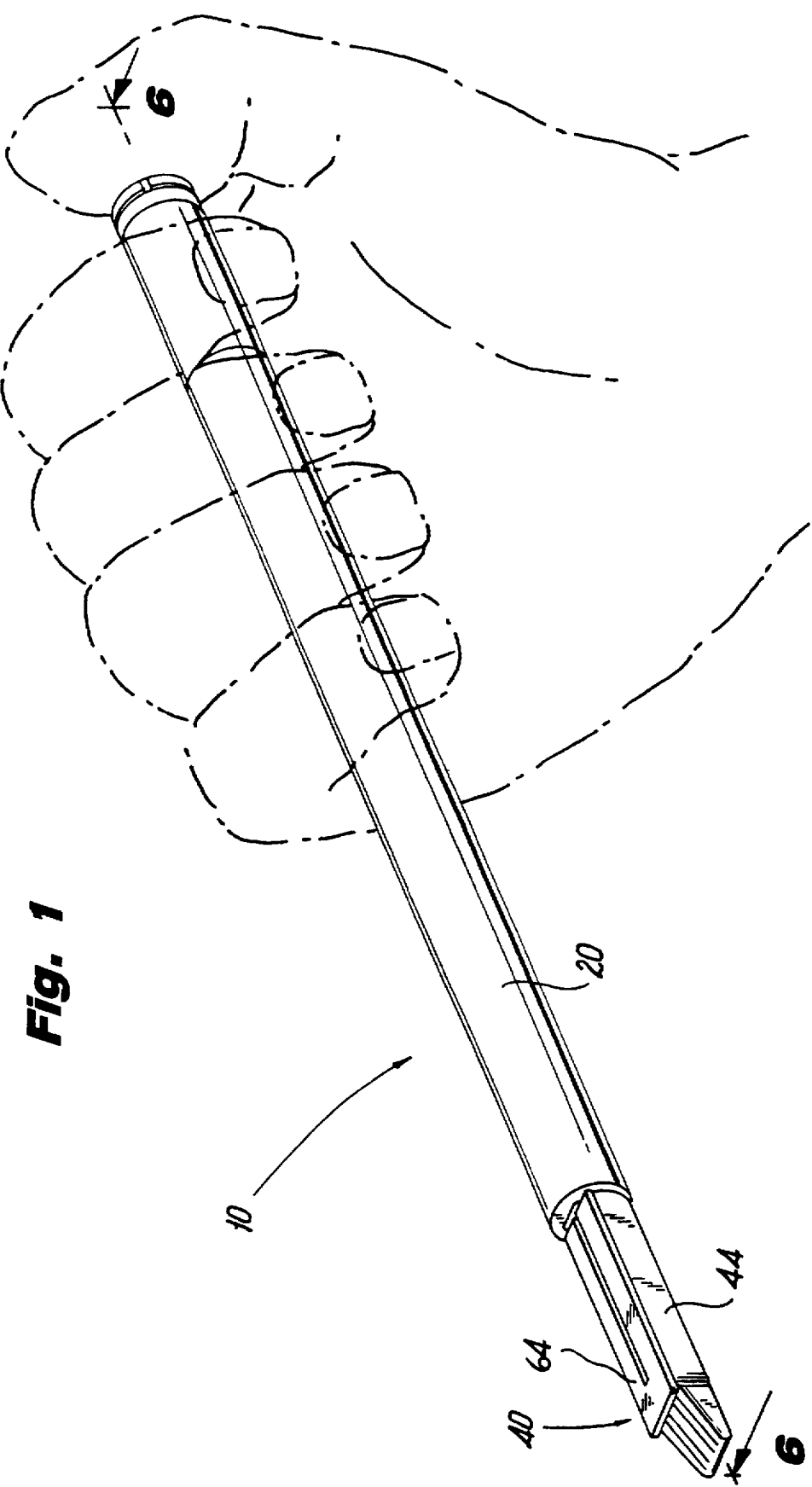
FIG. 1 is a perspective view of a powered stapling device constructed in accordance with a preferred embodiment.

In the drawings and in the description which follows, the term "proximal", as is traditional, will refer to the end of the apparatus which is closest to the operator, while the term "distal" will refer to the end of the apparatus which is furthest from the operator.

The apparatus shall be discussed in terms of both conventional and endoscopic procedures. However, use herein of terms such as "endoscopic", "endoscopically", and "endoscopic portion", among others, should not be construed to limit the present apparatus for use only in conjunction with an endoscopic tube. To the contrary, it is believed that the present apparatus may find use in procedures wherein access is limited to a small incision including but not limited to arthroscopic and/or laparoscopic procedures.

Referring now to the drawings wherein like reference numerals identify similar structural elements of the apparatus, there is illustrated in FIG. 1 a self-contained powered surgical stapler constructed in accordance with a preferred embodiment and designated generally by reference numeral 10.

Figure 2A:
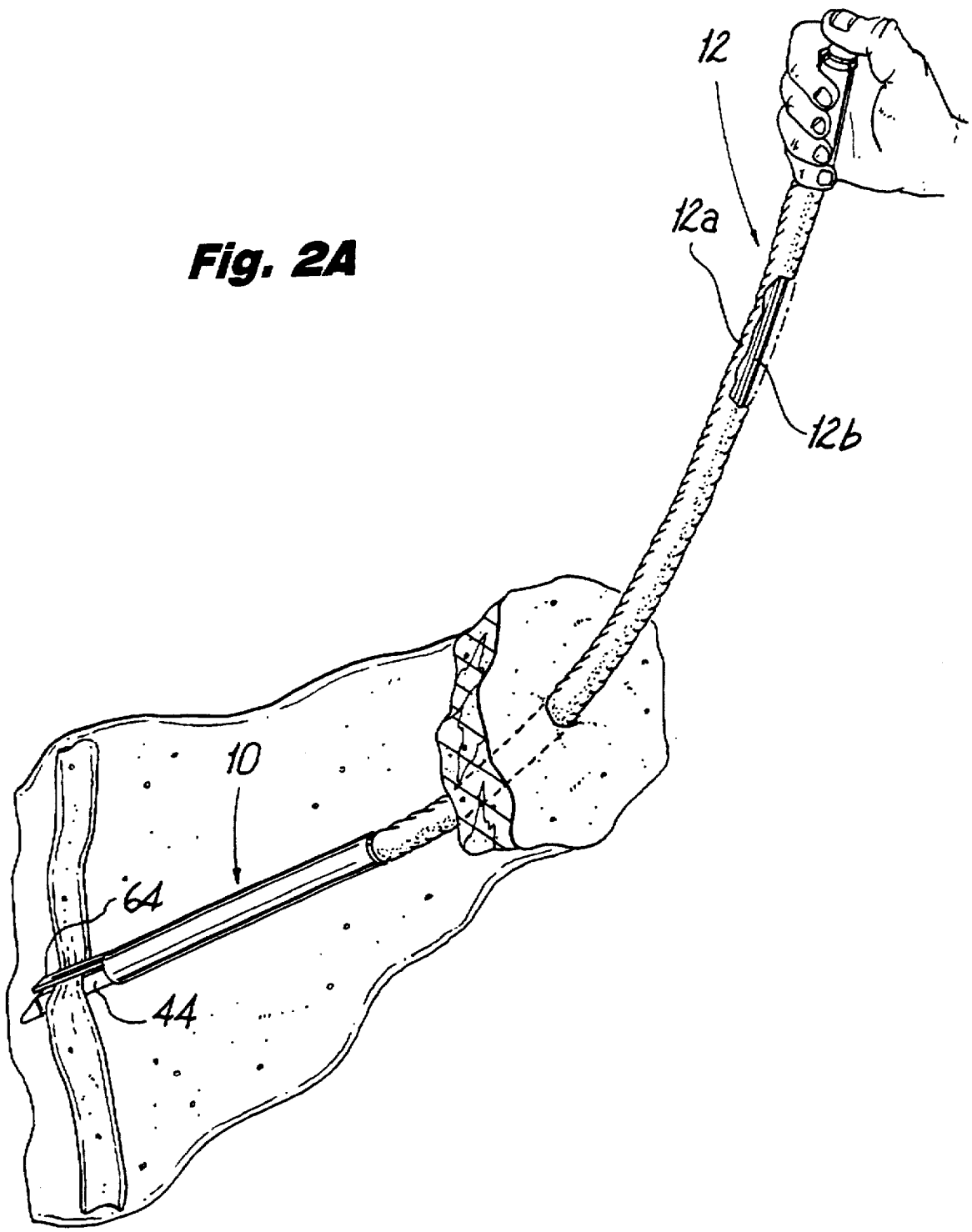
FIG. 2A is an illustration depicting the powered stapling device of FIG. 1 with a flexible extension shaft attached thereto in use during a laparoscopic procedure.
Figure 2B:
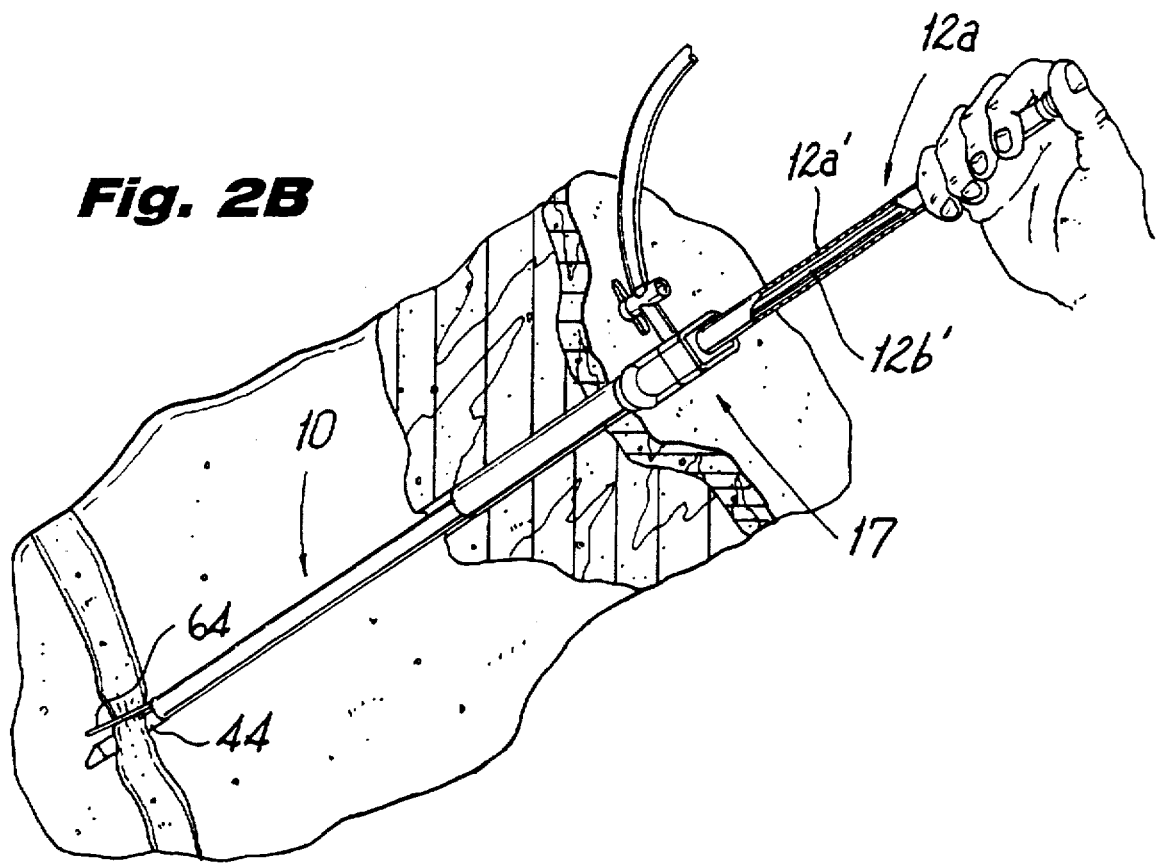
FIG. 2B is an illustration depicting the powered stapling device of FIG. 1 with a rigid extension shaft attached thereto in use during a laparoscopic procedure.

Referring to FIG. 1, powered surgical apparatus 10 is configured for use as a hand-held device for applying a plurality of surgical staples to tubular vessels and body tissue during conventional invasive surgical procedures. By way of example only, surgical apparatus 10 may have a length measuring from about 5.0 inches to about 7.0 inches, and an outer diameter of about 0.450 inches to about 0.500 inches. Preferably, the length of surgical apparatus 10 is between 6.0 inches and 6.5 inches, while the preferred diameter is between 0.470 inches and 0.480 inches. Clearly, other dimensions are contemplated. In one embodiment, surgical apparatus 10 is also adapted for use in endoscopic procedures through remote actuation from a location outside the patients body, as shown in FIGS. 2A and 2B. This is achieved by providing an elongated extension shaft 12 which attaches to the proximal end of surgical apparatus 10 by commonly known connective methods such as snap fit. Extension shaft 12 is preferably dimensioned and configured for insertion through a cannula or trocar device and has a length measuring from about 10.0 inches to about 17.0 inches. A flexible shaft 12 or rigid shaft 12' can be utilized.

Figure 3:
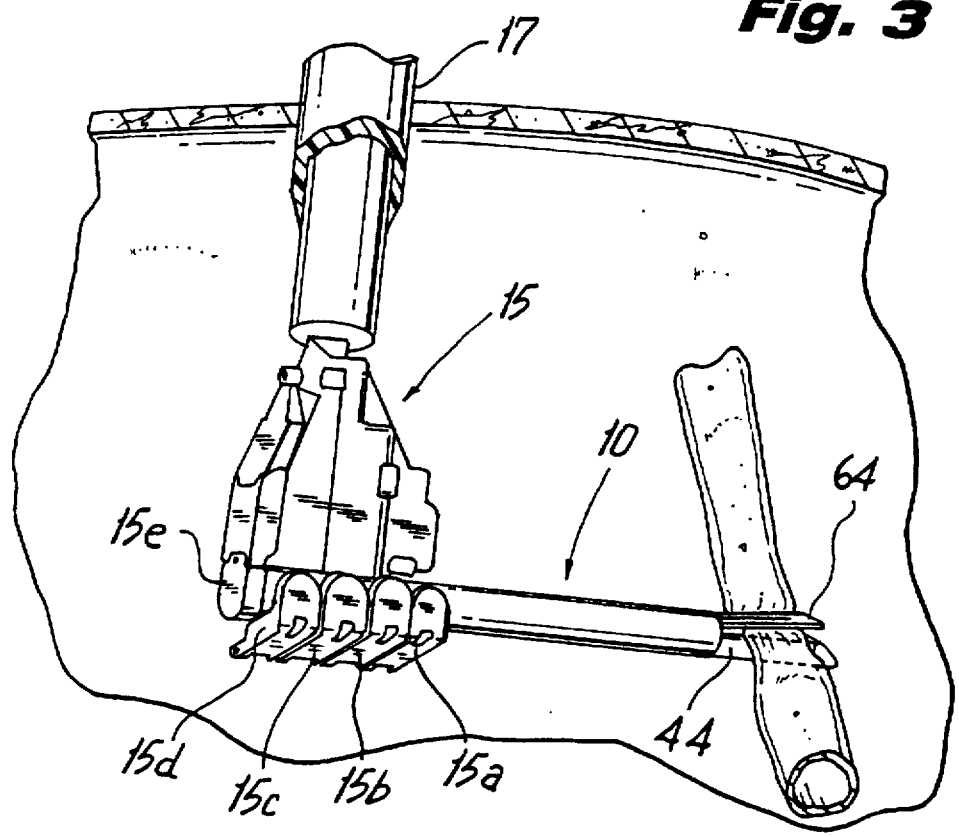
FIG. 3 is an illustration depicting a mechanical hand operating the powered stapling device of FIG. 1 during a laparoscopic procedure.

Referring to FIG. 3, in another embodiment, surgical apparatus 10 is intended to be operated by a mechanical hand 15 which is configured to extend through trocar device 17 during a laparoscopic surgical procedure. Mechanical hand 15 includes four articulated fingers 15a–15d and an opposable thumb 15e which are hinged together to enable relative movement between a constricted position wherein the forehand and fingers are drawn together into a narrowed formation to facilitate their extension through trocar 17 and a relaxed position wherein the forehand and fingers are deployed into a spread position to perform dexterous tasks such as operating surgical apparatus 10 by actuating a switch provided on the apparatus.

Figure 4:
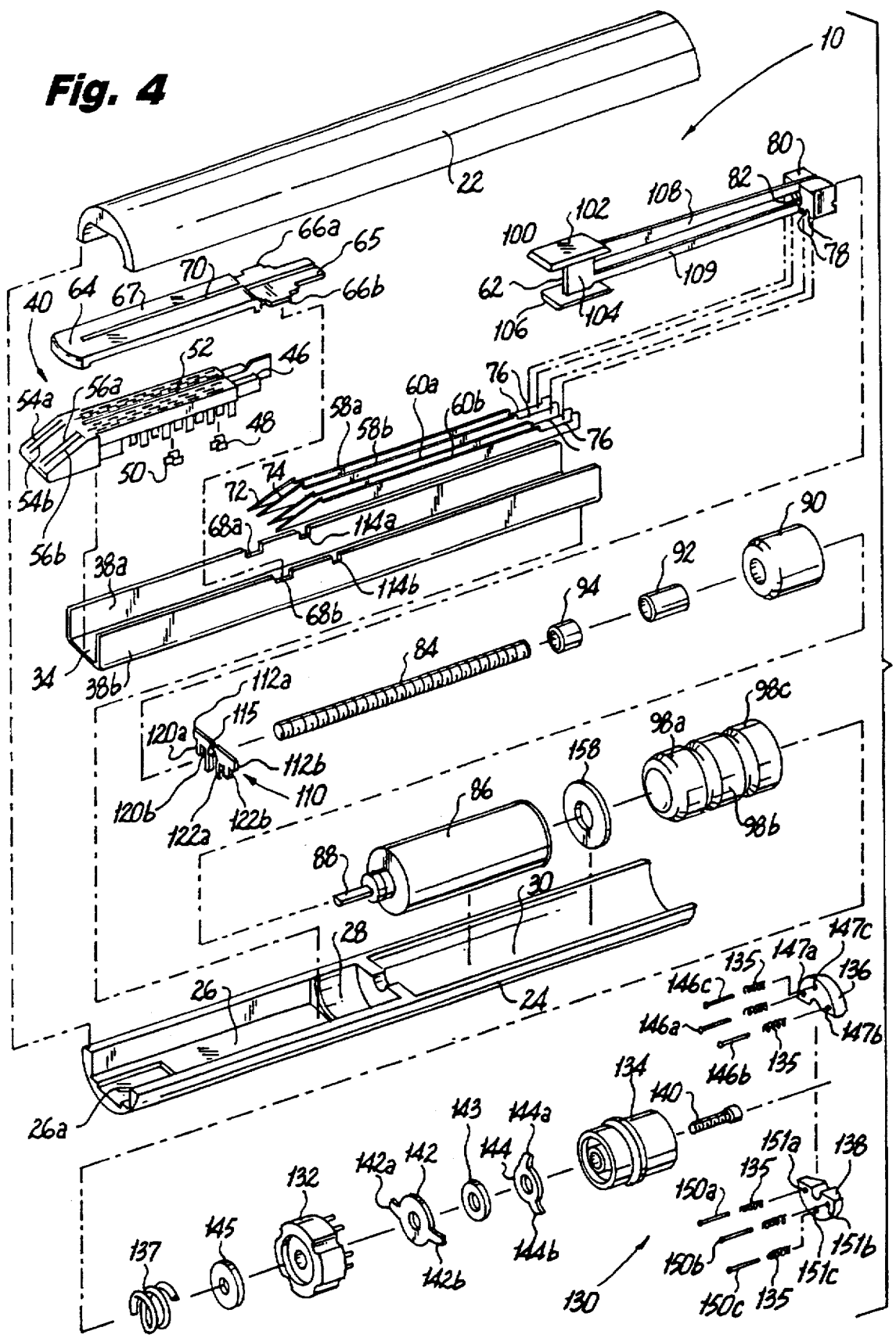
FIG. 4 is an exploded perspective view of the powered stapling device of FIG. 1.

Referring to FIG. 4, surgical apparatus 10 includes an elongate body 20 including complimentary body sections 22 and 24 which define a series of internal chambers for housing and supporting various mechanical components of apparatus 10. The internal chambers defined within body sections 22 and 24 include distal chamber 26, medial chamber 28, and proximal chamber 30.

The components housed within body sections 22 and 24 of surgical apparatus 10 include an elongate housing channel 32 having a base 34 and opposed upstanding channel walls 38a and 38b. Housing channel 32 is maintained within the distal chamber 26 of body 20 and is configured to support the assembly 40 and the actuating assembly 42.

The assembly 40 includes an elongate staple cartridge 44 having a plurality of transverse slots 46 each configured to support a respective staple 48 and staple pusher 50. Cartridge 44 is also provided with five spaced apart longitudinal slots including a central slot 52 and lateral slot pairs 54a, 54b and 56a, 56b. The lateral slot pairs 54a, 54b and 56a, 56b serve to accommodate longitudinal translation of the elongate camming bars 58a, 58b and 60a, 60b of actuating assembly 42 while the central slot 52 serves to accommodate longitudinal translation of a cutting blade 62. Actuating assembly 42 and the components associated therewith will be described in greater detail hereinbelow.

Assembly 40 further includes an elongate anvil 64 which defines an interior fastener forming surface 65 against which staples are driven when ejected from cartridge 44 by the actuating assembly 42. A pair of outwardly depending wings 66a and 66b are formed adjacent the proximal end of anvil 64 for engaging a pair of correspondingly positioned reception slots 68a and 68b formed in the opposed upstanding channel walls 38a and 38b of housing channel 32. The engagement of wings 66a and 66b within slots 68a and 68b facilitates pivotal movement of anvil 64 with respect to cartridge 44. A longitudinal slot 70 extends along a substantial portion of the length of anvil 64 to accommodate the longitudinal translation of cutting blade 62 and the portion of actuating assembly 42 which supports the cutting blade. Similarly, a longitudinal slot 75 is formed in the base 34 of housing channel 32 (see FIG. 6). The orientation and length of slots 70 and 75 correspond substantially to that of the central slot 52 provided in cartridge 44.

A spring 65 extends from the proximal end of anvil 64 and is attached to body section 22 (or alternatively base 34) to bias the anvil towards the cartridge 44. Thus, in use, as tissue is positioned between the anvil and cartridge, the anvil is forced away from the cartridge by the tissue. Actuation of the actuating assembly (discussed below) forces anvil 64 into closer cooperative alignment with cartridge 44 to more firmly and progressively clamp the tissue. In an alternate embodiment, the anvil 64 is biased to an open position, i.e. biased away from cartridge 44, by, for example, a pair of springs positioned at a proximal end of the anvil between the anvil and cartridge 44. It is also contemplated that the anvil can be connected for free movement with respect to the cartridge without a spring bias.

As best seen in FIG. 4, actuating assembly 42 includes two pairs of elongate camming bars 58a, 58b and 60a, 60b. The camming bars serve to sequentially eject staples 48 from cartridge 44 through interaction with staple pushers 50. In particular, each of the elongate camming bars includes a distal head portion 72 having an angled camming surface 74. Camming surface 74 is configured to contact staple pushers 50 and drive the staple pushers in a direction transverse to the longitudinal axis of cartridge 44, thereby urging the staples from cartridge 44. An engagement notch 76 is formed adjacent the proximal end of each of the camming bars for engaging corresponding grooves 78 provided in drive member 80.

Figure 9:
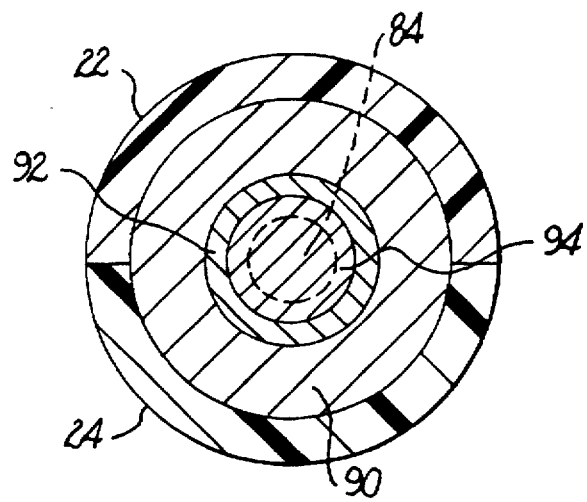
FIG. 9 is a cross-sectional view taken along line 9—9 of FIG. 6 illustrating the drive shaft of the motor assembly.
Figure 10:
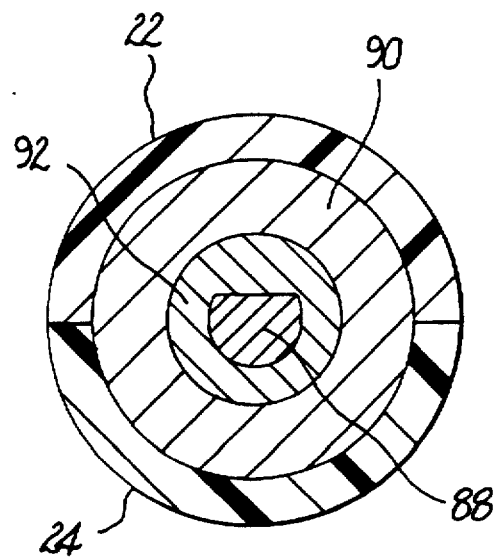
FIG. 10 is a cross-sectional view taken along line 10—10 of FIG. 6 illustrating the interaction between the drive shaft of the motor assembly and the axial drive screw.

Drive member 80 includes a threaded bore 82 for operatively engaging an axial drive screw 84. Drive screw 84 is driven by a motor assembly 86 and is connected to the drive shaft 88 of motor assembly 86 by a supporting hub assembly which includes an outer support hub 90, an intermediate support hub 92, and an inner engagement hub 94 (see FIG. 9). Engagement hub 94 is fastened to the proximal end of drive screw 84 and is engaged within the intermediate support hub 92. As shown in FIG. 10, drive shaft 88 is keyed into the opposed end of support hub 92. Support hub 92 is coaxially disposed within outer support hub 90 which is maintained with the medial chamber 28 of elongate body 20. Motor assembly 86 and the power cells 98a–9c which supply energy thereto are maintained with the proximal chamber 30 of elongate body 20. A transfer plate 158 is disposed between the distal-most power cell 98a and the proximal end of motor assembly 86 for transferring energy from the power cell to the motor assembly.

Actuating assembly 42 further includes a camming beam 100 for effectuating the progressive closure of anvil 64 to clamp body tissue disposed between fastener forming surface 65 of anvil 64 and the tissue contacting surface 45 of staple cartridge 44. Camming beam 100 includes an upper beam portion 102, a central web portion 104, and a lower beam portion 106. Central web portion 104 supports cutting blade 62. Upper and lower beam extensions 108 and 109 extend proximally from central web portion 104 to engage drive member 80. As shown, the upper and lower beam portions 102, 106 are substantially planar. Thus, the mechanism for clamping the anvil (camming beam 100) and the mechanism for firing the staples from the cartridge (camming bars 58a, 58b and 60a, 60b) are directly connected to drive member 80. In use, the upper beam portion 102 of camming beam 100 progressively contacts the outer surface 67 of anvil 64 to effect progressive anvil closure. The central web 104 translates through slots 52, 70, and 75, and the lower beam portion 106 translates along the outer surface 35 of the base 34 of housing channel 32 to maintain anvil closure during a stapling procedure.

Figure 8:
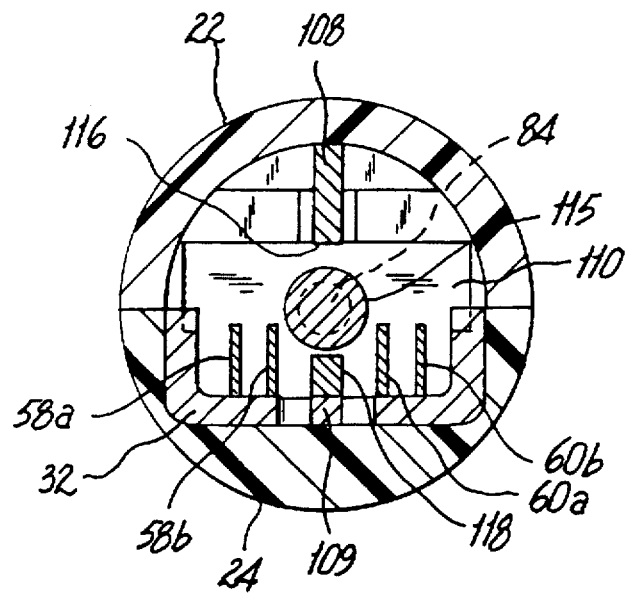
FIG. 8 is a cross-sectional view taken along line 8—8 of FIG. 6 illustrating the actuating assembly.

Referring to FIG. 8 in conjunction with FIG. 4, a support gate 110 is mounted intermediate housing channel 32 which has an aperture 115 for supporting the distal end portion of axial drive screw 84. As best seen in FIG. 4, support gate 110 includes a pair of opposed winglets 112a and 112b for engaging corresponding reception slots 114a and 114b in the opposed channel walls 38a and 38b of housing channel 32. Upper and lower grooves 116 and 118 are formed in support gate 110 to accommodate the translation of the upper and lower beam extensions 108 and 109. Lateral slot pairs 120a, 120b and 122a, 122b are provided in support gate 110 to accommodate the translation of camnming bar pairs 58a, 58b and 60a, 60b.

Surgical apparatus 10 further includes a switching assembly 130 for selectively controlling the operation of motor assembly 86. Switching assembly 130 includes distal and proximal switch housings 132 and 134, and right and left spring biased actuation buttons 136 and 138. A plurality of coiled compression springs 135 bias actuation buttons 136 and 138 in a proximal direction. Switch housings 132 and 134 are mounted to one another and fastened to the proximal end of surgical apparatus 10 by a threaded connector 140, and are operatively separated from one another by a distal insulating ring 141, a distal contact plate 142, a medial insulating ring 143, and a proximal contact plate 144. A distal contact ring 145 is disposed between distal switch housing 132 and spring 137.

Distal contact plate 142 includes a pair of opposed upturned contact tabs 142a and 142b, and proximal contact plate 144 includes a pair of opposed upturned contact tabs 144a and 144b which are positioned 60° out of phase with tabs 142a and 142b. Each actuation button has associated therewith three contact pins, two of which interact with contact plates 142 and 144 to control the relative movement of drive screw 84. In particular, actuation button 136 includes two long pins 146a and 146b and one short pin 146c. Short pin 146c is seated within a central reception port 147c, while long pins 146a and 146b are seated within lateral reception ports 147a and 147b.

Long pin 146a and short pin 146c are positioned to selectively engage contact tabs 142a and 144b respectively, while long pin 146b remains free from electrical contact. Similarly, actuation button 138 includes long pins 150a and 150b, and short pin 150c. Short pin 150c is seated within a central reception port 151c, while long pins 150a and 150b are seated within lateral reception ports 151a and 151b. Long pin 150b and short pin 150c are positioned to selectively engage contact tabs 142b and 144b respectively, while long pin 150a remains free from electrical contact.

Figure 5:
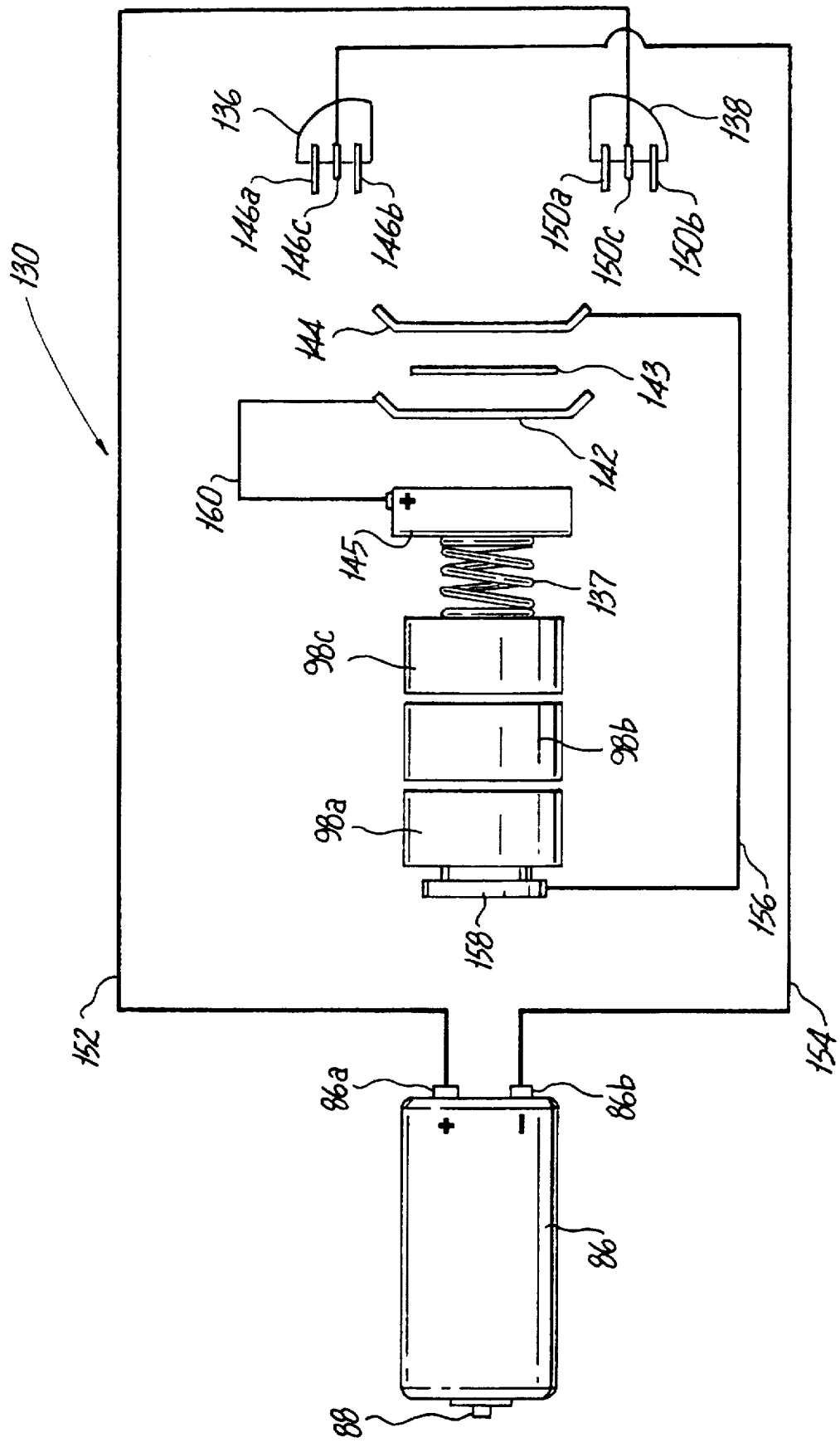
FIG. 5 is a schematic representation of the switching mechanism for controlling the operation of the motor assembly.

The wiring configuration of switching assembly 130 is illustrated in FIG. 5 and includes motor line 152 which interconnects the positive terminal 86a of motor assembly 86 to contact pins 146a and 150c, and a motor line 154 which interconnects the negative terminal 86b of motor assembly 86 to contact pins 146c and 150b. In addition, a transmission line 156 extends between battery transfer plate 158 and contact plate 144, and a transmission line 160 interconnects contact plate 142 and contact ring 145.

In use, when actuation button 138 is depressed, long pin 150b contacts tab 142b of distal contact plate 142 and short pin 150c contacts tab 144b of proximal contact plate 144. Thus, the positive terminals of power cells 98a–98c will be connected to the negative terminal 86b of motor assembly 86 and the negative terminals of power cells 98a–98c will be connected to the positive terminal 86a of motor assembly 86, causing drive shaft 88 to rotate in a clockwise direction to move drive member 80 distally. When actuation button 136 is depressed, long pin 146a contacts tab 142a of distal contract plate 142 and short pin 146c contacts tab 144a proximal contact plate 144. Thus, the positive terminals of power cells 98a–98c will be connected to the positive terminal 86a of motor assembly 86 and the negative terminals of power cells 98a–98c will be connected to the negative terminal 86b of motor assembly 86, causing drive shaft 88 to rotate in a counter-clockwise direction to move the axial drive member 80 in a proximal direction. It is also envisioned that a single actuator button can be provided which will be actuable to operate an axial drive screw having a reverse thread formed therein. The reverse thread will cause a distally translating drive screw to automatically translate in a proximal direction at the conclusion of a fastener forming stroke.

As discussed briefly hereinabove, surgical apparatus 10 is preferably designed for insertion through a trocar or cannula device to apply surgical staples to body tissue located within a body cavity while being actuable remote from the surgical site. Shaft 12 includes elongate transmission members 12a and 12b (or 12a' and 12b') for effectuating remote actuation of switching assembly 130 (see FIGS. 2A and 2B). Transmission members 12a and 12b (or 12a' and 12b') may include a pair of substantially rigid rods for transmitting a mechanical signal to actuation buttons 136 and 138, or, in the alternative, the transmission members may include transmission cables for directing an electrical signal to switching assembly 130. In either instance, the shaft would include two actuation buttons to respectively actuate buttons 136 and 138 and cause the rotation of drive screw 84 in opposed directions.

Figure 6:
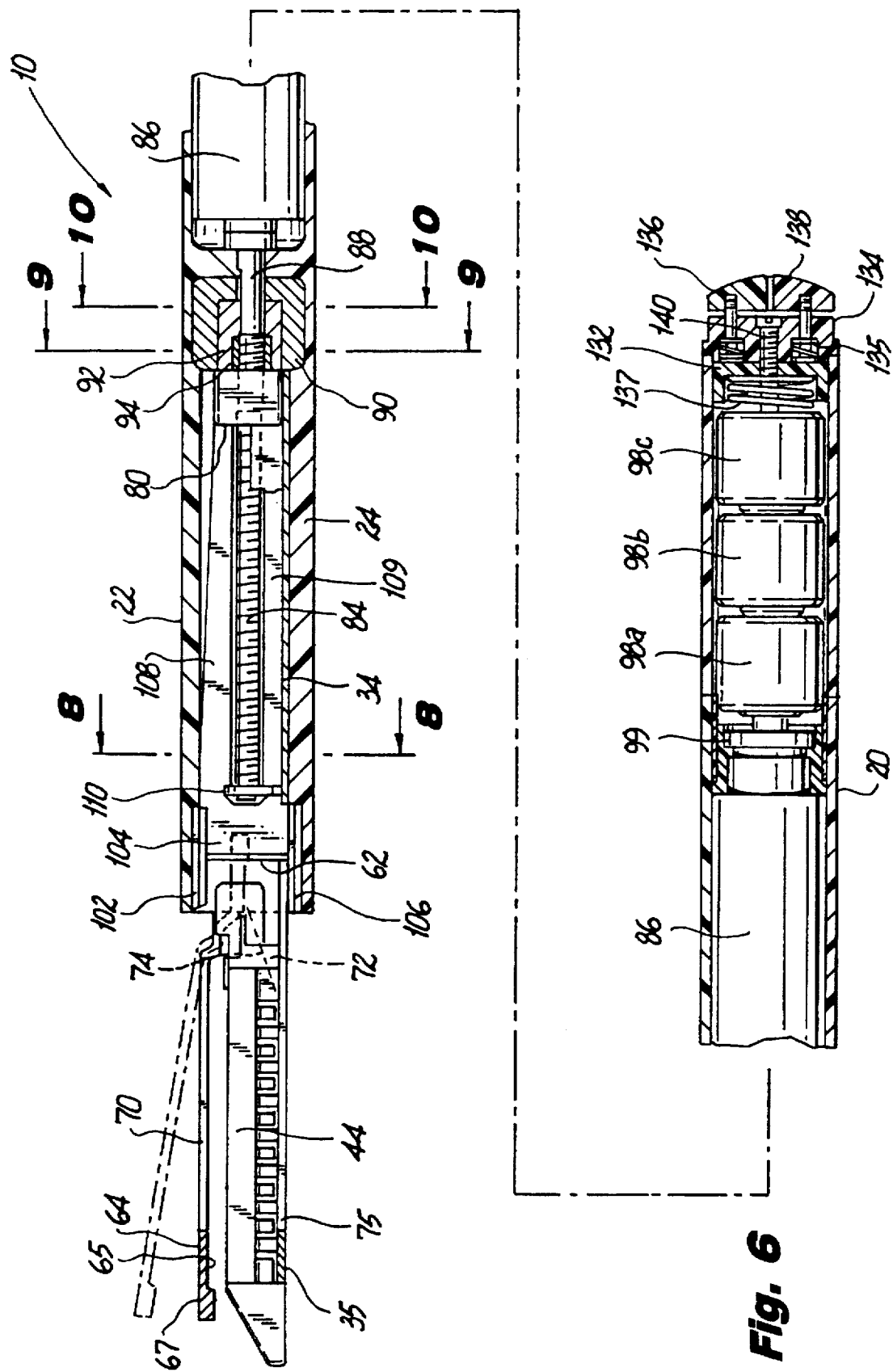
FIG. 6 is a side elevational view in cross-section taken along line 6—6 of FIG. 1 illustrating the relative position of the internal components of the powered stapling device prior to actuation.
Figure 7:
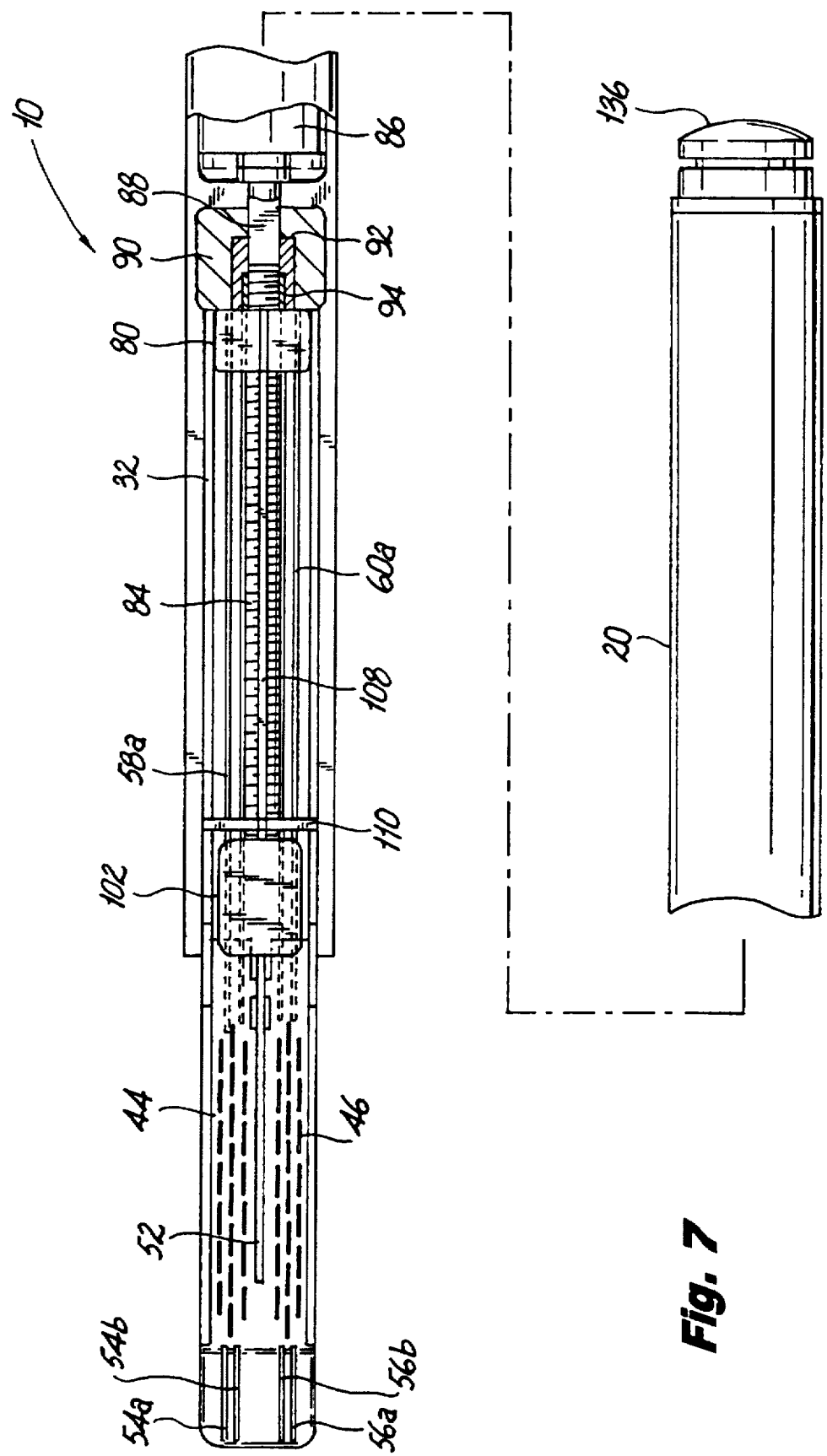
FIG. 7 is a top plan view in cross-section illustrating the relative position of the internal components of the powered stapling device prior to actuation.

Referring now to FIGS. 6 and 7, prior to operating the surgical stapling device 10, the anvil 64 is disposed in a free-movement position to facilitate the capture of body tissue (or spring biased to a closed or an open position as in the aforementioned alternate embodiments). Movement of anvil 64 is accommodated by the pivotal engagement of anvil wings 66a and 66b in reception slots 68a and 68b. The pivotal movement of anvil 64 is best seen in FIG. 6. Prior to actuation, camming beam 100 is maintained within a support seat 26a defined in the distal chamber 26 of instrument body 20. At such a time, the upper beam portion 102 is out of contact with the outer surface 67 of anvil 64 permitting the pivotal movement thereof. Also at this time, the distal head portion 72 of each of the camming bars 58a, 58b and 60a, 60b is disposed proximal to and out of contact with the proximal-most staple pushers 50 in cartridge 44.

Figure 11:
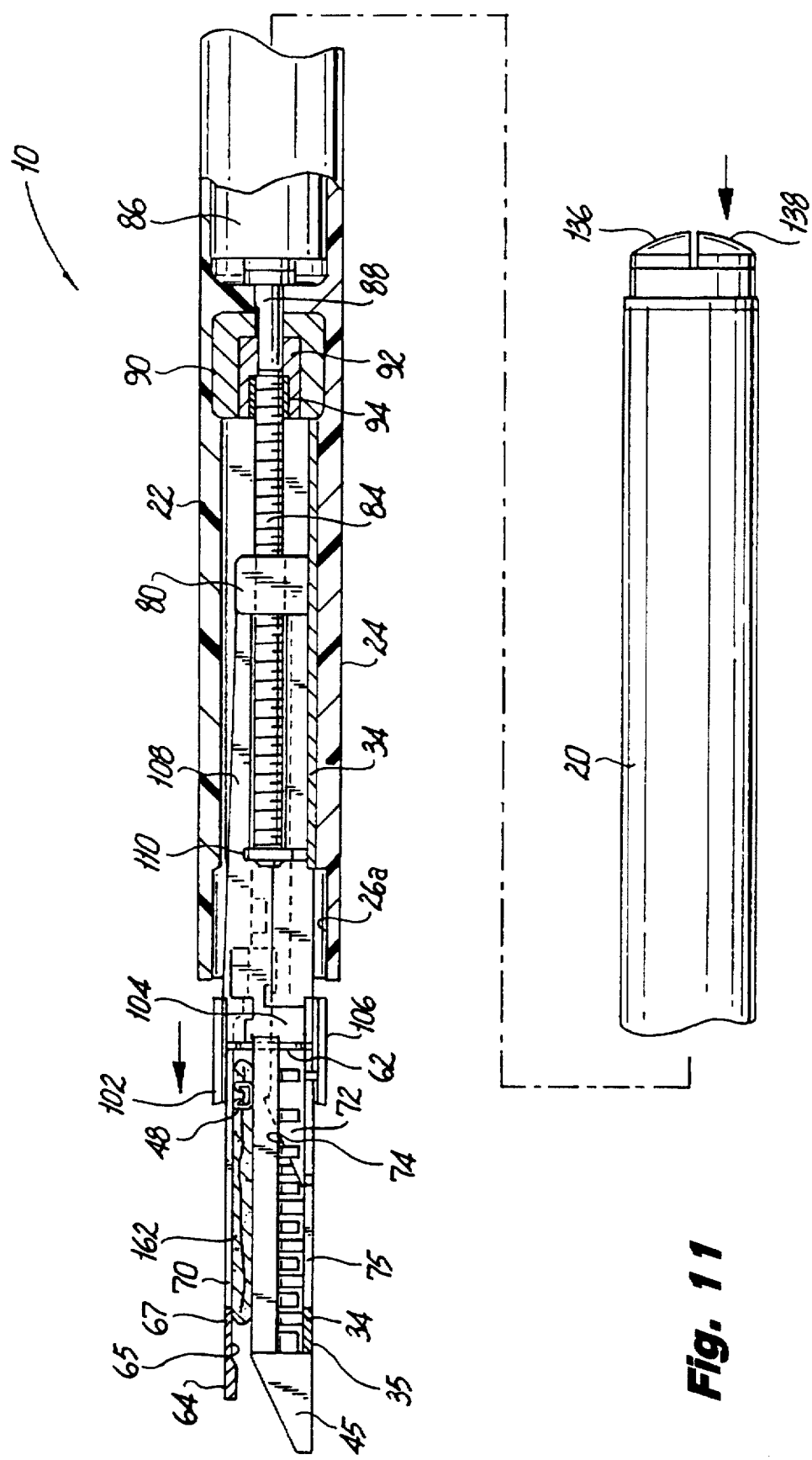
FIG. 11 is a side elevational view in cross-section illustrating the relative position of the internal components of the powered stapling device during a stapling operation.
Figure 12:
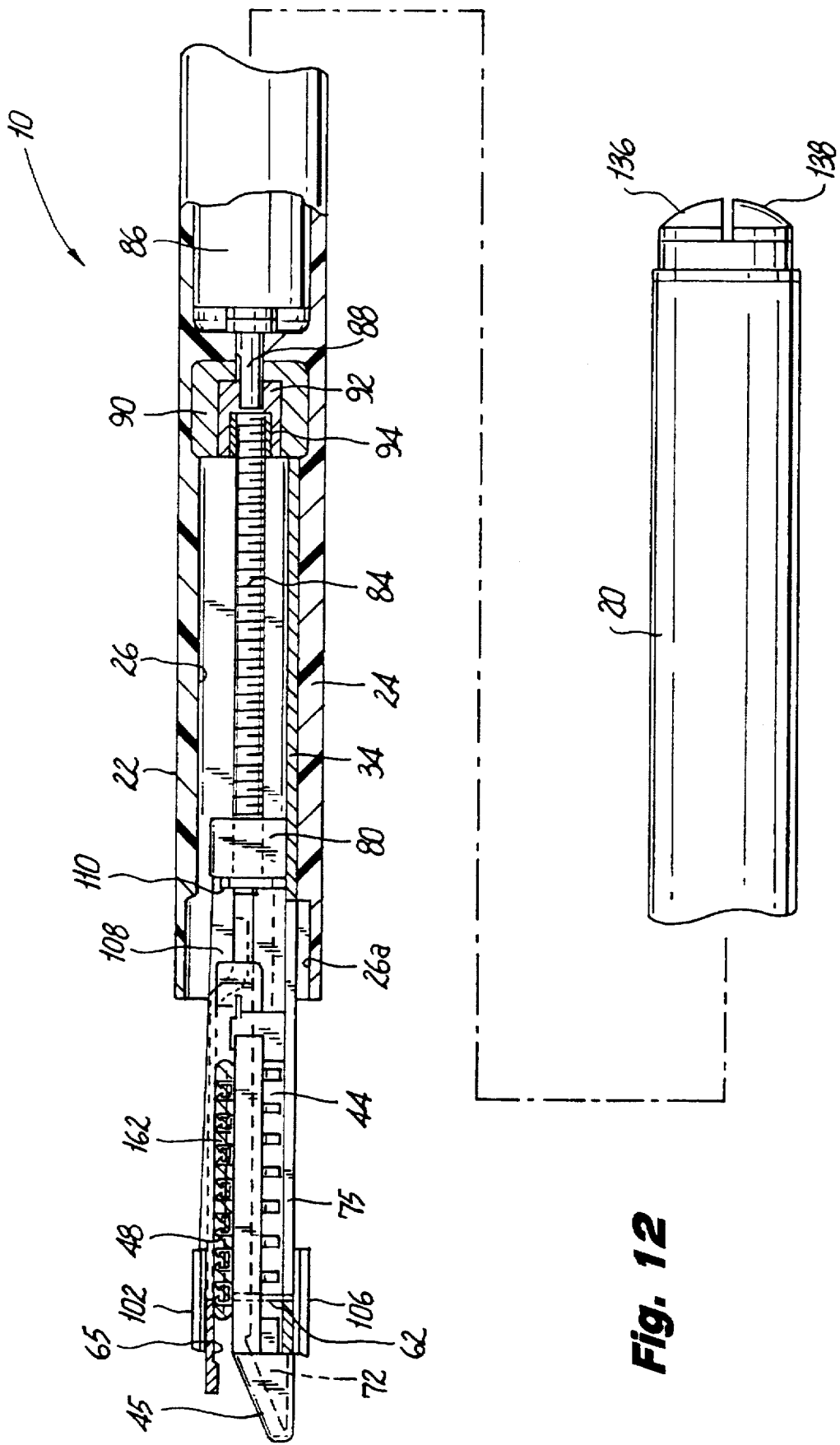
FIG. 12 is a side elevational view in cross-section illustrating the relative position of the internal components of the powered stapling device at the completion of a stapling operation.

Upon actuation, i.e. when actuation button 136 is depressed, motor assembly 86 is energized and drive shaft 88 rotates axial drive screw 84, causing drive member 80 to translate in a distal direction. As best seen in FIG. 11, as drive member 80 translates distally, the upper beam portion 102 of camming beam 100 progressively urges anvil 64 toward cartridge 44 to clamp body tissue 165 therebetween. Concomitantly, the camming surface 74 on the distal head portion 72 of each of the camming bars of actuation assembly 42 interacts with staple pushers 50 to sequentially eject surgical staples 48 from cartridge 44.

Staples ejected from cartridge 44 are driven through body tissue 165 and formed against the inner fastener forming surface 65 of anvil 64. As the rows of staples are placed in body tissue 165, cutting blade 62, which travels behind the distal head portion 72 of each of the camming bars of actuation assembly 42, cuts the stapled body tissue, forming an incision between the staple rows.

Continued actuation of motor assembly 86 effects distal translation of drive member 80 until the drive member contacts support gate 110. At such a time, camming beam 100 is disposed at the distal end of fastener applying assembly 40 and the distal head 70 of each of the camming bars is disposed within the distal portion 45 of staple cartridge 44. Following the stapling operation, depression of actuation button 138 causes drive member 80 to translate proximally, drawing therewith camming beam 100 and camming bars 58a, 58b and 60a, 60b to their proximal-most position (FIG. 6).

It is also contemplated that the staple cartridge 44 can be removable so that once actuation assembly 42 has returned to its proximal-most position after firing the fasteners, staple cartridge 44 can be removed and replaced with a loaded staple cartridge and actuation button 136 can be depressed again to fire the stapling apparatus.

Figure 13:
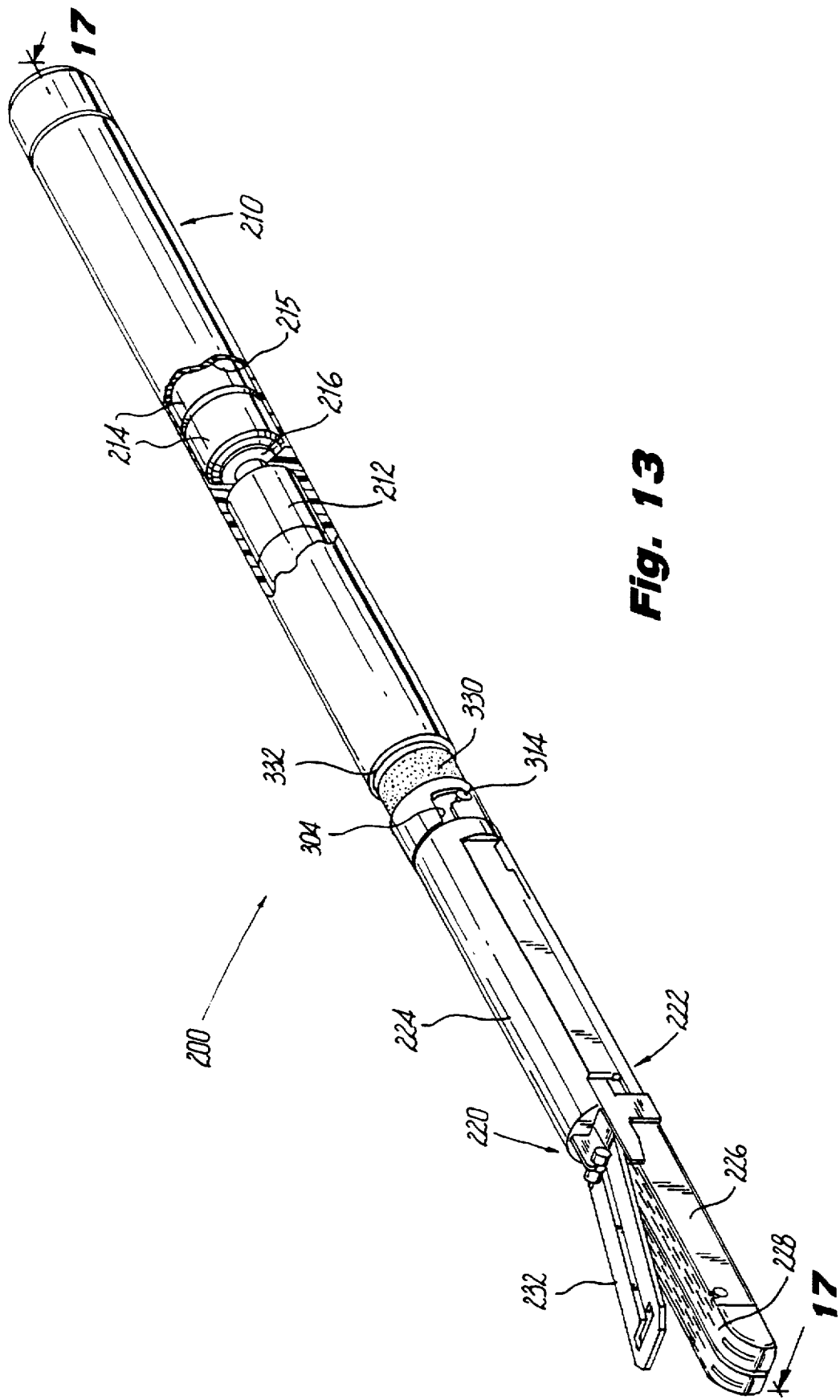
FIG. 13 is a perspective view of another powered stapling device constructed in accordance with a preferred embodiment of the subject application which includes a detachable cartridge assembly that can be discarded after a stapling operation.

Referring now to FIG. 13, there is illustrated another self-contained powered surgical apparatus constructed in accordance with a preferred embodiment of the subject application and designated generally by reference numeral 200. Surgical apparatus 200 is configured to sequentially apply a plurality of surgical fasteners to body tissue during conventional and/or endoscopic surgical procedures. In brief, surgical apparatus 200 includes an elongate instrument body 210 and a disposable cartridge assembly 220 which is detachably connected to a distal end portion of the instrument body 210 by a bayonette-type coupling arrangement. Instrument body 210 houses a motor assembly 212 and a plurality of power cells or batteries 214 for energizing the motor assembly. The power cells can be lithium, alkaline or nickel-cadmium batteries. An insulating material is wrapped around the power cells to isolate them from conductive outer casing 215. A conductive contact plate 216 is disposed between the terminal end 212a of motor assembly 212 and the distal-most battery 214a, and a coiled spring 218 is disposed within the proximal end of instrument body 210 to bias the batteries distally (see FIG. 17).

Figure 14:
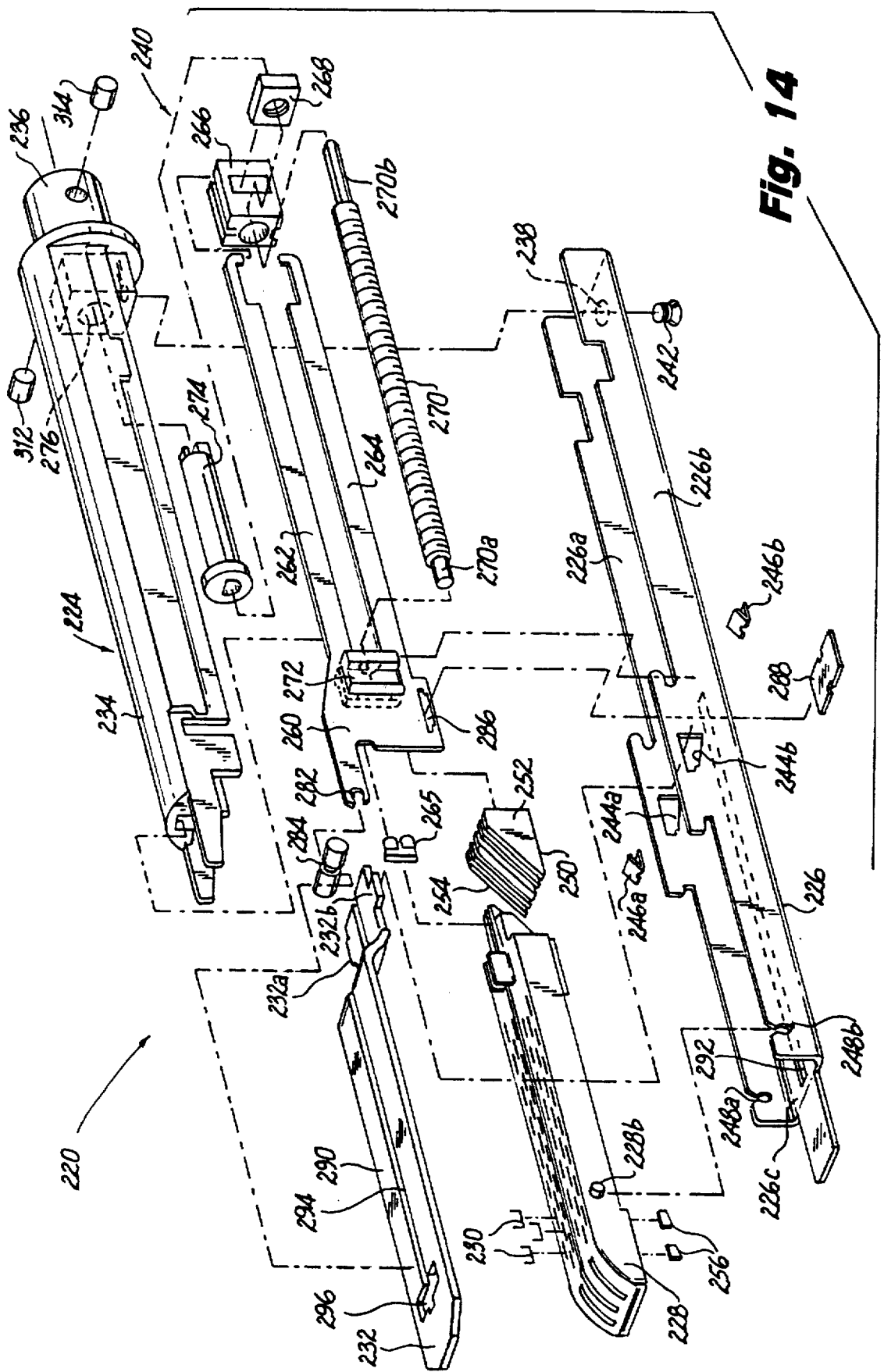
FIG. 14 is an exploded perspective view of the detachable cartridge assembly illustrated in FIG. 13.

Referring to FIGS. 13 and 14, cartridge assembly 220 includes a frame 222 having an adapter 224 configured to detachably engage a distal end portion of instrument body 210 (see generally FIG. 16), and a housing channel 226 configured to retain a cartridge 228 containing a plurality of surgical fasteners 230. Cartridge assembly 220 further includes an anvil 232 which is pivotably mounted to housing channel 226, and an actuation assembly designated generally by reference numeral 240 which is driven by motor assembly 212 and configured to eject the surgical fasteners 230 from cartridge 228, and concomitantly move anvil 232 between an open position and a closed position (see generally FIGS. 18 and 19).

With continuing reference to FIG. 14, adapter 224 includes an elongate distal portion 234 and a proximal mounting portion 236 dimensioned and configured for reception within the distal end of instrument body 210. Housing channel 226 includes opposed side walls 226a and 226b, and a floor 226c. An aperture 238 is defined in floor 226c adjacent the proximal end of housing channel 226 for receiving a threaded fastener 242 which mounts the housing channel 226 to the adapter 224. A pair of opposed apertures 244a and 244b are defined in the side walls 226a and 226b of housing channel 226 for receiving a pair of outwardly extending flanges 232a and 232b which are formed adjacent the proximal end of anvil 232 and about which anvil 232 pivots between closed and opened positions to capture and release body tissue. A pair of spring members 246a and 246b are disposed within apertures 244a and 244b for biasing anvil 232 into an open position. Opposed engagement notches 248a and 248b are also defined in the opposed side walls 226a and 226b of housing channel 226 for receiving a pair of corresponding detents formed on cartridge 228, i.e. detent 228b. The detents are formed monolithically with the fastener retaining cartridge 228 and secure the cartridge within the distal portion of housing channel 226.

With continuing reference to FIG. 14, the actuation assembly 240 of cartridge assembly 220 includes an actuation sled 250 configured to translate through cartridge 228 to effectuate the ejection of surgical fasteners therefrom. Sled 250 includes a plurality of spaced apart upstanding cam plates 252 each having an angled leading edge 254 for sequentially engaging a plurality of staple drivers 256 which drive surgical fasteners 230 from cartridge 228. Actuation sled 250 is driven through cartridge 228 by an actuation beam 260 and an axial drive screw 270. Actuation beam 260 has a pair of parallel elongate beam extensions 262 and 264 the proximal ends of which are mounted to a follower housing 266. Follower housing 266 supports a drive nut 268 which is threadably associated with axial drive screw 270. Follower housing 266 is mounted within frame 222 in such a manner so that axial rotation of drive screw 270 causes the longitudinal translation thereof. The distal end 270a of drive screw 270 is rotatably supported in a stationary support mount 272 which is maintained within frame 222 and engaged in a slotted region 235 of the distal portion of adapter 234. Support mount 272 also serves to guide the longitudinal translation of beam extensions 262 and 264 as actuation beam 260 is driven in a longitudinal direction by follower housing 266. A knife blade 265 is mounted adjacent the leading edge of actuation beam 260 for cutting body tissue as actuator 250 translates through cartridge 228.

Figure 15:
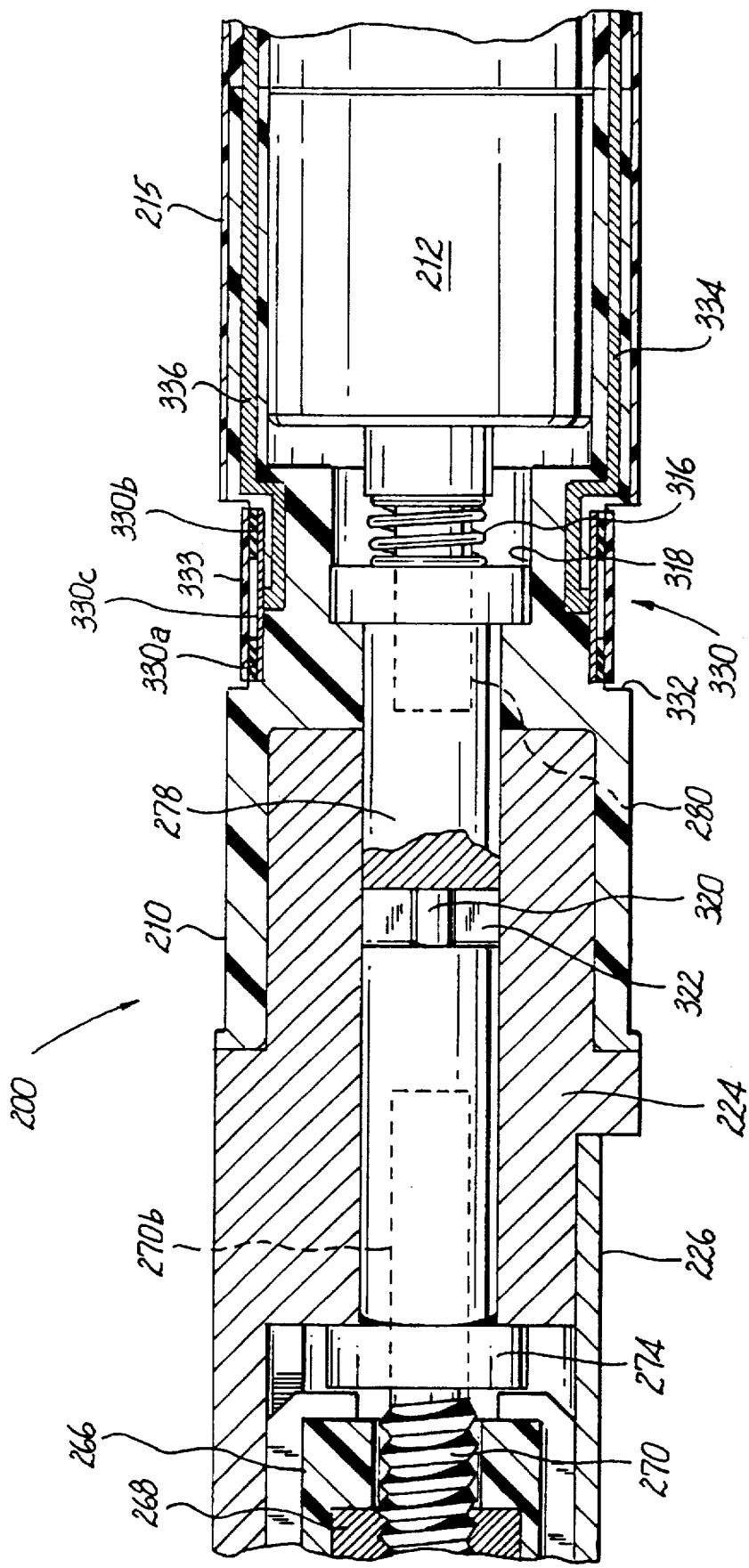
FIG. 15 is an enlarged side elevational view in cross section of a portion of the stapling device of FIG. 13 illustrating the coupling engagement of the axial drive screw of the cartridge assembly and the axial drive shaft of the motor assembly.
Figure 16:
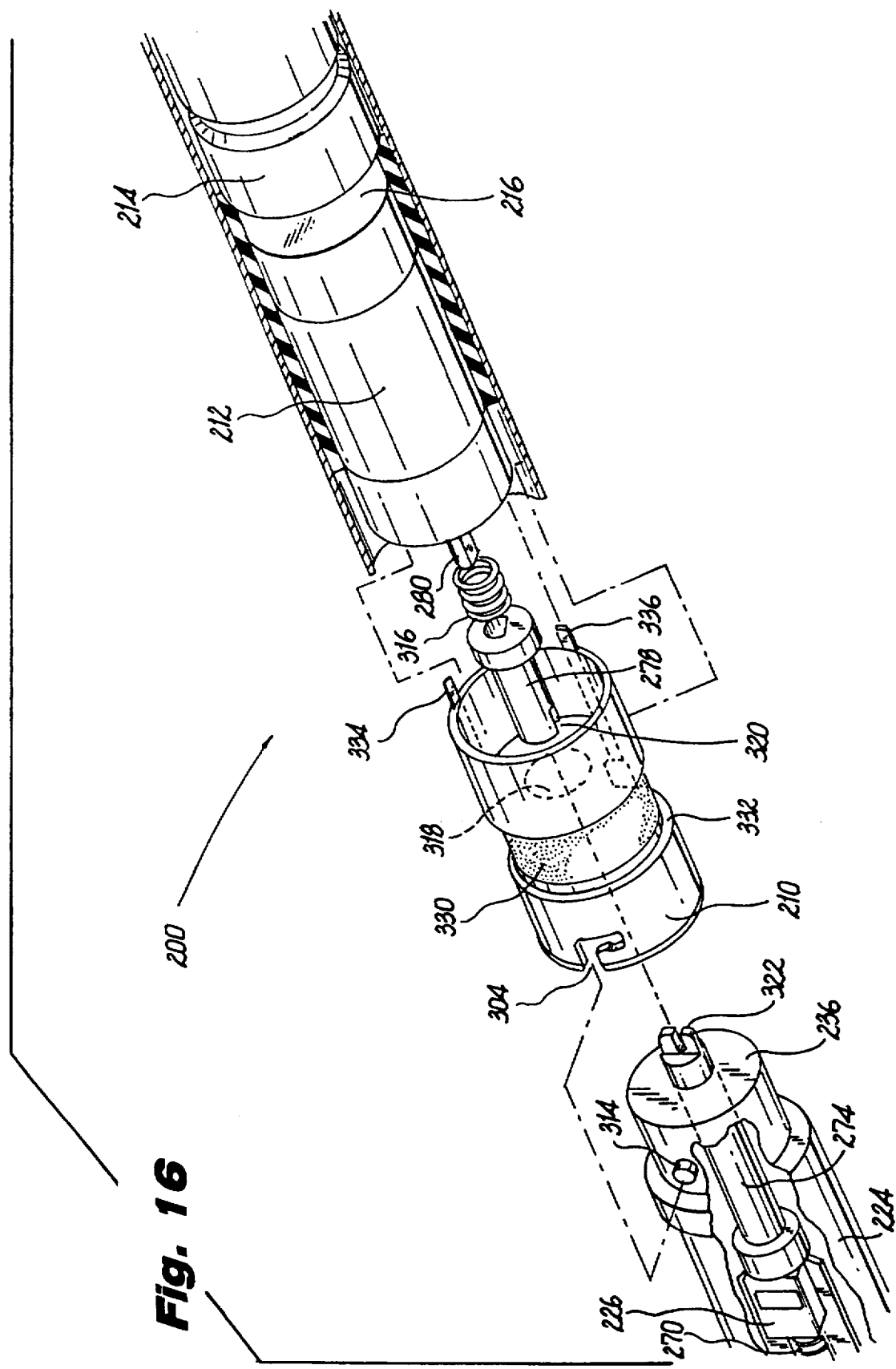
FIG. 16 is an exploded perspective view in partial cross-section illustrating the components of the stapling deceive which facilitate the detachable connection of the cartridge assembly and the instrument body.

Referring to FIGS. 14–16, the proximal end 270b of drive screw 270 is configured to engage a screw coupling 274. Screw coupling 274 is rotatably supported within an axial bore 276 defined in the proximal mounting portion 236 of adapter 224 and is detachably connected at a proximal end to a shaft coupling 278 which is supported on the drive shaft 280 of motor assembly 212. The cooperative engagement of the two couplings will be discussed in greater detail hereinbelow.

Referring once again to FIG. 14, the distal end of actuation beam 260 include a retention flange 282 for supporting a generally cylindrical cam roller 284 and an engagement slot 286 for retaining a substantially planar cam beam 288. Cam roller 284 engages and translates relative to an upper camming surface 290 of anvil 232 to effectuate the progressive closure thereof as follower housing 266 and actuation beam 260 translate through housing channel 226 to fire surgical fasteners 230 from cartridge 228. Cam beam 288 engages and translates relative to the outer surface of the floor 226c of housing channel 226 to balance the forces exerted upon anvil 232 by cam roller 284 during closure. A longitudinal slot 292 is defined in the floor 226c of housing channel 226 and a corresponding longitudinal slot 294 is defined in the anvil 232 to accommodate the longitudinal translation of actuation beam 260. A transverse slot extension 296 is defined at the distal end of anvil slot 294 to receive cam roller 284 at the end of its translation, and thereby permit anvil 232 to return to an open position under the bias of spring members 246a and 246b following a fastening operation. Thus, body tissue is automatically unclamped as soon as all of the fasteners have been fired.

Referring now to FIGS. 13 and 16, as noted hereinabove, the cartridge assembly 220 of surgical apparatus 200 is configured as a separate unit which is detachably mounted to the distal end of the instrument body 210 by a bayonette-type coupling arrangement. The bayonette coupling arrangement includes a pair of generally J-shaped slots 304 defined adjacent the distal end of instrument body 210, and a pair of corresponding engagement pins 312 and 314 mounted in the proximal mounting portion 234 of adaptor 224 (see also FIG. 14). During attachment of cartridge assembly 220, the proximal mounting portion 236 of adapter 224 is axially rotated approximately 20 degrees to engage pins 312 and 314 in corresponding slots 302, 304.

Figure 17:
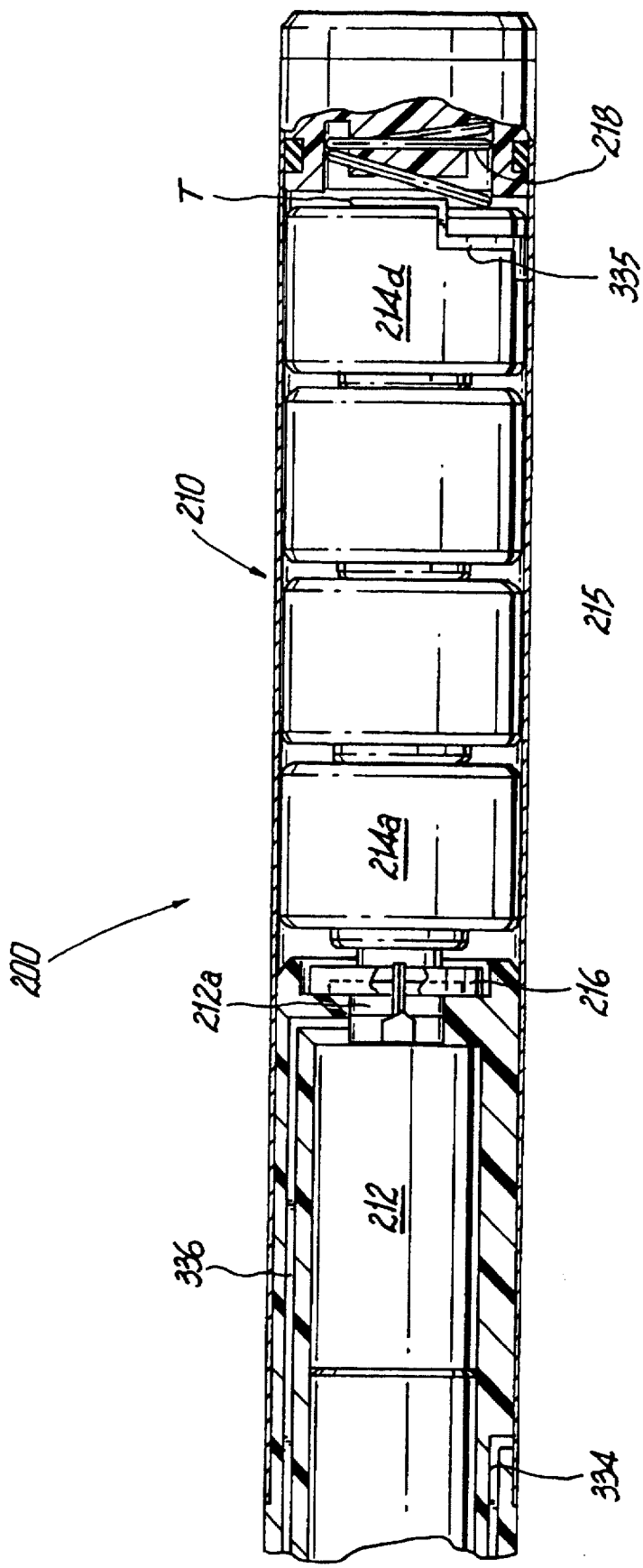
FIG. 17 is a side elevational view in cross-section taken along line 17—17 of FIG. 13 illustrating the motor assembly and power cells housed within the elongate body of the surgical apparatus of FIG. 13.

Referring to FIGS. 16 and 17, a coiled compression spring 316 is supported on the drive shaft 280 of motor assembly 212 for biasing the shaft coupling 278 in a distal direction. Shaft coupling 278 is supported within a stepped axial bore 318 defined in instrument body 210 and includes a transverse slot 320 which is dimensioned and configured to engage a corresponding teeth 322 formed at the proximal end of screw coupling 274. The function of coupling spring 316 is two fold. Firstly, if teeth 322 and flange 322 are not aligned when the proximal mounting portion of adapter 224 is inserted into the distal end of instrument body 210, coupling spring 316 will compensate for the misalignment and facilitate engagement of the couplings upon initial rotation of drive shaft 280. More particularly, upon insertion of the adapter, if misaligned, teeth 322 will abut the distal-most surface of shaft coupling 278. When drive shaft 280 initially rotates and slot 320 aligns with flange 322, coupling spring 316 will decompress and force shaft coupling 278 in a distal direction to cause the two couplings to detachably engage. The second function of coupling spring 316 is to bias adapter 224 in a distal direction when the bayonette coupling which detachably maintains cartridge assembly 220 in body portion 210 is engaged.

Referring to FIGS. 15–17, a switch 330 is provided for selectively controlling the operation of motor assembly 212. Switch 330 is a touch-sensitive contact switch that is wrapped around the circumference of instrument body 210 within a recessed area 332. Switch 330 includes an outer contact layer 330a, a medial insulating layer 330b, and an inner conductive layer 330c. A slot 333 is provided in insulating layer 330b to permit contact between the outer contact layer 330a and the inner conductive layer 330c. A motor control circuit is defined by a first electrically conductive metallic strip 334 which connects switch 330 to the conductive outer casing 215 of instrument body 210, a second conductive strip 235 which connects outer casing 215 to the terminal T of the proximal-most power cell 214d, and a third conductive strip 336 which connects switch 330 to the terminal end 212a of motor assembly 212.

Figure 18:
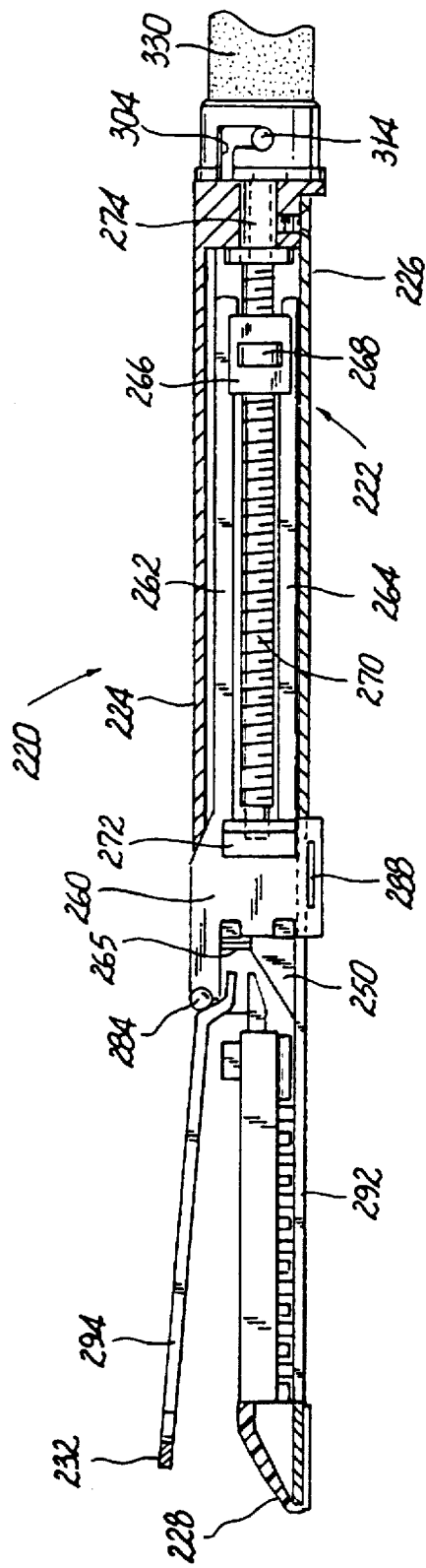
FIG. 18 is a side elevational view in cross-section taken along line 17—17 of FIG. 13 illustrating the cartridge assembly of the subject application prior to a stapling operation.
Figure 19:
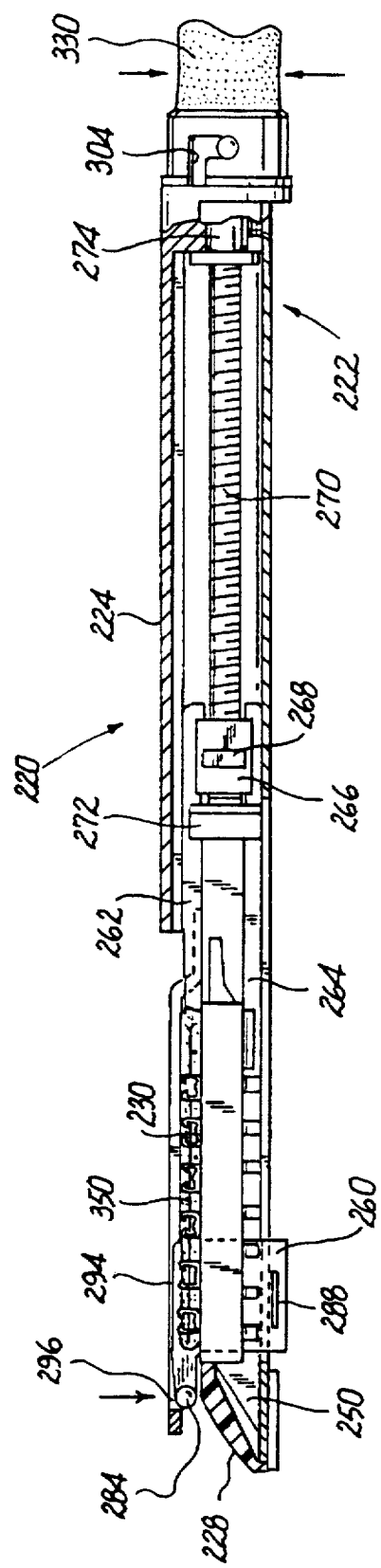
FIG. 19 is a side elevational view in cross-section taken along line 17—17 of FIG. 13 illustrating the cartridge assembly of the subject invention at the conclusion of a stapling operation.

Referring now to FIGS. 18 and 19, in operation, when surgical apparatus 200 is introduced into a surgical site, body tissue is captured between anvil 232 and cartridge 228. A radially inwardly directed force in two locations on switch 330 brings outer layer 330a into contact with inner layer 330c, then causing current to flow to motor assembly 212 to rotate the drive shaft 280 of motor assembly 212. The rotational motion of drive shaft 280 is transferred to drive screw 270 through couplings 274 and 278. Axial rotation of drive screw 270 causes corresponding longitudinal translation of follower housing 266 and actuation beam 260.

As actuation beam 260 translates distally, cam roller 284 progressively moves anvil 232 from the normally biased open position shown in FIG. 18 to the closed position illustrated in FIG. 19. Concomitantly, actuation sled 250 is driven from the proximal position illustrated in FIG. 18, through fastener retention cartridge 228, to the distal-most position shown in FIG. 19 sequentially engaging staple drivers 256 so as to drive surgical fasteners 230 through body tissue 350. At the same time, knife blade 265 trails actuation sled 250 to form an incision in the stapled body tissue 350. When cam roller 284 reaches the distal end of longitudinal slot 294, it drops into transverse slot extension 296, permitting anvil 232 to return to an open position and release the stapled body tissue 350. At the conclusion of the fastener applying operation, cartridge assembly 212 is manipulated in such a manner so as to disengage pins 312 and 314 from slots 302 and 304, and detach the cartridge adapter 224 from the distal end of instrument body 210. Thereafter, the cartridge assembly may be discarded and a new cartridge assembly may be detachably mounted to instrument body 210.

Although the apparatus has been described with respect to preferred embodiments, it will be readily apparent to those having ordinary skill in the art to which it appertains that changes and modifications may be made thereto without departing from the spirit or scope of the appended claims.

What is claimed is:

1. A self-contained powered surgical apparatus for applying surgical fasteners to body tissue comprising:
   a) an elongate body defining a longitudinal axis;
   b) a cartridge assembly detachably supported in a distal end portion of the elongate body, and including:
      i) a frame having a proximal end portion configured to engage the distal end portion of the elongate body;
      ii) a housing supported within the frame and containing a plurality of surgical fasteners;
      iii) an anvil pivotably associated with the frame and mounted for movement with respect to the housing between an open position and a closed position;
      iv) an actuation assembly configured to translate in a longitudinal direction relative to the housing and the anvil to progressively move the anvil from the open position to the closed position and to sequentially eject the surgical fasteners from the housing to be formed against the anvil; and
      v) an axial drive screw rotatably mounted within the frame and threadably associated with the actuation assembly for effectuating the longitudinal translation thereof;
   c) a motor assembly disposed within the elongate body and including an axial drive shaft;
   d) a coupling disposed within the elongate body for detachably connecting the axial drive shaft of the motor assembly and the axial drive screw of the cartridge assembly; and
   e) a power source disposed within the elongate body for energizing the motor assembly.

2. A powered surgical apparatus as recited in claim 1, wherein a bayonet-type fitting is associated with the distal end portion of the elongate body and the proximal end portion of the frame to facilitate detachable engagement of the cartridge assembly.

3. A powered surgical apparatus as recited in claim 2, wherein the bayonet-type fitting includes a generally J-shaped slot defined in one of the distal end portion of the elongate body and the proximal end portion of the frame, and a corresponding engagement pin provided on the other of the distal end portion of the elongate body and the proximal end portion of the frame.

4. A powered surgical apparatus as recited in claim 1, further comprising an actuation switch for selectively controlling the operation of the motor assembly.

5. A powered surgical apparatus as recited in claim 4, wherein the actuation switch is disposed proximate an intermediate portion of the elongate body.

6. A powered surgical apparatus as recited in claim 1, wherein the coupling is spring biased in a distal direction.

7. A powered surgical apparatus as recited in claim 1, wherein the anvil is spring biased into the open position.

8. A powered surgical apparatus as recited in claim 1, wherein the anvil includes an inner fastener forming surface against which fasteners are driven when ejected from the housing, and an opposed outer camming surface.

9. A powered surgical apparatus as recited in claim 8, wherein the actuation assembly includes a cam roller dimensioned and configured to engage the outer camming surface of the anvil to effect the progressive closure thereof.

10. A self-contained powered surgical apparatus for applying surgical fasteners to body tissue comprising:
 a) an elongate body defining a longitudinal axis;
 b) a disposable cartridge assembly detachably supported in a distal end portion of the elongate body, and including:
  i) a frame having opposed distal and proximal end portions;
  ii) a housing supported within the distal end portion of the frame and containing a plurality of surgical fasteners;
  iii) an anvil pivotably associated with the frame and mounted for movement with respect to the housing between an open position and a closed position;
  iv) an actuation assembly configured to translate in a longitudinal direction relative to the housing and the anvil to progressively move the anvil from the open position to the closed position and to sequentially eject the surgical fasteners from the housing to be formed against the anvil; and
  v) an axial drive screw rotatably mounted within the proximal end portion of the frame and threadably associated with the actuation assembly for effectuating the longitudinal translation thereof;
 c) means for detachably connecting the proximal end portion of frame and the distal end portion of the elongate body;
 d) a motor assembly disposed within the elongate body and including an axial drive shaft;
 e) means for detachably connecting the axial drive shaft of the motor assembly and the axial drive screw of the cartridge assembly; and
 f) a power source disposed within the elongate body for energizing the motor assembly.

11. A powered surgical apparatus as recited in claim 10, wherein the means for detachably connecting the frame to the elongate body comprises a bayonet-type fitting.

12. A powered surgical apparatus as recited in claim 11, wherein the bayonet-type fitting includes a generally J-shaped slot defined in the distal end portion of the elongate body, and a corresponding engagement pin provided on the proximal end portion of the frame.

13. A powered surgical apparatus as recited in claim 10, wherein the means for detachably connecting the axial drive shaft and the axial drive screw comprises a coupling member disposed within the elongate body.

14. A powered surgical apparatus as recited in claim 13, further comprising a coiled compression spring for biasing the coupling member in a distal direction.

15. A disposable cartridge assembly for a surgical apparatus configured to sequentially apply a plurality of surgical fasteners to body tissue, the apparatus including an elongated body and an actuator mounted for axial rotation within the elongated body, the cartridge assembly comprising:
 a) an elongate housing defining a longitudinal axis and containing a plurality of surgical fasteners;
 b) a frame supporting the housing and configured to be detachably mounted to a distal end portion of the elongated body of the apparatus;
 c) an anvil associated with the frame and mounted for pivotal movement with respect to the housing between an open position and a closed position;
 d) an actuation assembly configured to translate in a longitudinal direction relative to the housing and the anvil to progressively move the anvil from the open position to the closed position and to concomitantly sequentially eject surgical fasteners from the housing to be formed against the anvil; and
 e) an axial drive screw rotatably mounted within the frame and threadably associated with the actuation assembly for effectuating the translation thereof, whereby a proximal end of the drive screw is configured to detachably engage a distal end of the actuator such that axial rotation of the actuator causes corresponding longitudinal translation of the actuation assembly.

16. A disposable cartridge assembly as recited in claim 15, further comprising a cutting blade configured to translate through the cartridge assembly in conjunction with the actuation assembly to form an incision in stapled body tissue.

17. A disposable cartridge assembly as recited in claim 15, wherein the anvil is normally biased into the open position.

18. A disposable cartridge assembly as recited in claim 17, wherein the anvil includes an inner fastener forming surface against which fasteners are driven when ejected from the housing, and an opposed outer camming surface.

19. A disposable cartridge assembly as recited in claim 18, wherein the actuation assembly includes a cylindrical roller cam dimensioned and configured to engage the outer camming surface of the anvil to effect the progressive closure thereof as the actuation assembly translates in a longitudinal direction.

20. A disposable cartridge assembly as recited in claim 19, wherein a slot is defined in the anvil to receive the cam roller and permit the anvil to return to the normally biased open position at the conclusion of a fastening operation.

* * * * *